United States Patent [19]

Simons et al.

[11] Patent Number: 5,332,679
[45] Date of Patent: Jul. 26, 1994

[54] METHOD FOR SPECIFIC BINDING ASSAYS USING A RELEASABLE LIGAND

[75] Inventors: Donald M. Simons, Wilmington; Susan Y. Tseng, Hockessin, both of Del.; David M. Obzansky, Elkton, Md.

[73] Assignee: E. I. DuPont de Nemours and Company, Wilmington, Del.

[21] Appl. No.: 29,971

[22] Filed: Feb. 12, 1993

Related U.S. Application Data

[63] Continuation of Ser. No. 670,459, Mar. 12, 1991, abandoned.

[51] Int. Cl.$^5$ .................................... G01N 33/543
[52] U.S. Cl. ............................ 436/518; 435/7.5; 435/7.92; 435/7.93; 435/7.94; 436/501
[58] Field of Search ............... 435/6, 7.5, 7.92, 7.93, 435/7.94; 436/501, 518

[56] References Cited

U.S. PATENT DOCUMENTS

| | | | |
|---|---|---|---|
| 3,654,090 | 4/1972 | Schuurs et al. | 436/518 |
| 4,228,237 | 10/1980 | Hevey et al. | 435/7 |
| 4,231,999 | 11/1980 | Carlsson et al. | 424/1 |
| 4,271,140 | 6/1981 | Bunting et al. | 424/1 |
| 4,289,747 | 9/1981 | Chu | 435/7.8 |
| 4,298,685 | 11/1981 | Parikh et al. | 435/7 |
| 4,434,236 | 2/1984 | Freytag et al. | 436/512 |
| 4,535,057 | 8/1985 | Dreesman et al. | 435/5 |
| 4,659,678 | 4/1987 | Forrest et al. | 436/512 |
| 4,971,904 | 11/1990 | Luddy | 435/7 |

FOREIGN PATENT DOCUMENTS 0303229 2/1989 European Pat. Off. .

OTHER PUBLICATIONS

B. R. Clark et al, in E. T. Maggio (Ed.), Enzyme-Immunoassay, CRC Press, Inc., Boca Raton, Fla., 1980, pp. 167-173.

Hofmann et al. "Auidin Bonding of Carboxyl-Substituted Biotin and Analogues" Biochemistry, vol. 21, 1982 pp. 978-984.

Lichstein et al., Biochemical and Biophysical Research Communications 20(1):41-45 (1965).

Finn et al., Biochemistry, 23:2554-2558 (1984).

Ikariyama et al., Analytical Chemistry 57:495-500 (1985).

Primary Examiner—David Saunders

[57] ABSTRACT

Immunoassays and DNA probe assays utilizing a non-immune, reversible binding displacement system are provided. In the assay, a releasable ligand, a binding partner for the releasable ligand, an analyte of interest, an analytically detectable (reporter) group, and at least one binding partner for the analyte, are first attached to an insoluble phase so as to form reporter-labeled complex bound to an insoluble phase, followed by the addition of a displacer ligand which displaces the releasable ligand along with some portion of the reporter-labeled complex, so that the released reporter is analytically detectable in a free liquid medium and can be related to the concentration of analyte in the sample.

19 Claims, No Drawings

METHOD FOR SPECIFIC BINDING ASSAYS USING A RELEASABLE LIGAND

This is a continuation of application Ser. No. 07/670,459 filed Mar. 12, 1991, now abandoned.

TECHNICAL FIELD

This invention relates to specific binding assays, and more specifically to immunoassays and DNA probe assays which utilize a non-immune, reversible binding displacement system, in which a releasable ligand, a binding partner for the releasable ligand, an analyte of interest, an analytically detectable reporter, and at least one binding partner for the analyte, are first attached to an insoluble phase so as to form reporter-labeled complex bound to an insoluble phase, which is followed by the addition of a displacer ligand which displaces the releasable ligand along with some of the reporter-labeled complex, so that the released reporter is analytically detectable in a free liquid medium and can be related to the concentration of analyte in the sample.

BACKGROUND ART

In recent years, the use of the avidin-biotin complex has become well-known as am extremely versatile system, useful in a wide variety of bioanalytical applications including affinity chromatography, affinity cytochemistry, cell cytometry, blotting technology, diagnostics including immunoassays arid gene probe assays, hybridoma technology, bioaffinity sensors, drug delivery, and crosslinking, immobilization technology [Wilchek et al., Analytical Biochemistry 171:1-31 (1988)].

The usefulness of the biotin-avidin system is characterized in terms of the high affinity ($10^{15}$ M$^{-1}$) of the biotin-avidin interaction, which accounts for the exceptional stability of this non-covalent interaction. Free biotin, or biotin in derivatized form (containing any of a number of reporter groups including fluorescent, radioisotope, electron-dense marker, enzyme, or immobilizing matrices) or biotin coupled to either low or high molecular weight molecules, is still recognized by avidin or streptavidin.

There have been several well-known applications of the biotin-avidin system including its use in enzyme-labeled immunoassays. In all of these the detection signal is achieved either by using a reporter-labeled avidin or streptavidin or by using native avidin or streptavidin and a biotinylated reporter.

U.S. Pat. No. 4,298,686, issued to Parikh et al. on Nov. 3, 1981, discloses a quantitative method for the determination of biological substances. In particular, an enzyme immunoassay is disclosed which utilizes a soluble biotin-tagged complex, in which biotin is covalently attached to an antibody molecule and a separation process is performed using avidin, which is immobilized on a solid phase.

U.S. Pat. No. 4,228,237, issued to Hevey et al. on Oct. 14, 1980, discloses the use of a biotin-avidin system for the determination of a ligand of interest in non-competitive and competitive binding processes. In particular, Hevey et al. disclose a method for the determination of a ligand of interest which utilizes enzyme-labeled avidin and biotin-labeled reagent in a specific binding process wherein the ligand to be determined is contacted with an insoluble phase containing a specific binding substance for the ligand. Following the specific binding reaction, the enzyme activity of either the insoluble phase or the liquid phase is assayed and thereby related to the amount of ligand in the medium.

U.S. Pat. No. 4,271,140, issued to Bunting on Jun. 2, 1981, discloses the use of noncovalent binding systems in double receptor specific binding assays in which a first receptor is bound by a second receptor, with the first receptor being capable of reversibly binding either a ligand or another receptor.

U.S. Pat. No. 4,659,678, issued to Forrest et al. on Apr. 21, 1987 discloses an immunoassay for detection of an antigen in a liquid sample wherein a complex is formed between antigen contained in the sample and two or more antibody reagents, the complex is bound to a solid support by non-covalent bonding, so that the amount of complex becoming bound to the support is determined and the process employs at least one monoclonal antibody. The biotin-avidin system is described as an example of a high affinity bonding system useful in the invention.

There are a number of limitations of the avidin-biotin system in diagnostic assays. One limitation is due to the occurrence of nonspecific binding, generally attributed to the basicity of the reporter-labeled avidin or streptavidin. Typically, non-specifically bound components cannot be washed away from the solid support systems, which can include polystyrene, polyacrylamide, nylon, crosslinked dextran of nitrocellulose paper, glass beads, plastic tubes or microtitre plates. The resulting signal noise is especially troublesome when the component to be assayed is present in very low concentrations. Usually, streptavidin is used instead of avidin in order to minimize non-specific binding.

Another limitation of an avidin-biotin system is that its use is generally restricted to measurement of the analyte of interest while it is bound to a solid support. In those cases where the reporter is an enzyme, practical difficulties associated with measurement while the complex remains bound to the solid phase can occur. The advantage of measuring an enzyme-labeled immunocomplex in free solution is that it reacts much more rapidly with a substrate in free solution than when bound to a solid support because reaction in free solution is less diffusion-limited and less sterically hindered. This circumstance provides a great advantage when immunoassays are carried out in automated diagnostic systems. Further, immunoassays requiring measurement of an analytically detectable group bound to a solid phase may be limited in that they require the use of special types of solid supports, such as those that are colorless and transparent.

The problems associated with measuring a reporter-labeled immuno-complex bound to a solid support, as described in the preceding paragraph, have stimulated efforts directed at releasing the labeled immuno-complex from the support into free solution. One approach is to so devise the chemistry that the immuno-complex is attached to the solid support through a chemical structure that can be cleaved by a chemical reaction such as reduction, oxidation and hydrolysis. For example, U.S. Pat. 4,231,999, issued to Carlsson et al. on Nov. 4, 1980, discloses a reagent for use with an immunochemical assay which entails an improved conjugating technique based on thiol-disulfide exchange. The reagent is characterized by the fact that it comprises a soluble conjugate of one or more molecules of immunoglobulin and one or more units of an analytically detectable group, in which molecules and units are bound together via bridges containing the cleavable —S—S— group.

The use of chemically clearable bridges to attach immuno-complexes and the like to solid supports is elegant in concept but has proved to be of value only in special cases because the harsh conditions used to break the bridge may also cause damage elsewhere and thus reduce or destroy bioactivity required in the complex that is released. For this reason, the use of some non-covalent system involving a ligand and its binding partner as a bridge for joining components of an assay system, and a means of rapidly and gently displacing the ligand from its binding partner in order to subsequently separate the components of the assay system would be a more widely applicable technique.

Most applications of the biotin-avidin systems previously described are concerned only with tight and efficient binding. However, Hofmann et al. [Biochemistry 21: 978–984 (1982)] disclose that biotinyl-insulin and some of its analogs can bind non-covalently to succinoylavidin immobilized on AH Sepharose and can be released biospecifically by exposure of the loaded resin to buffers containing an excess of biotin. It may be noted here that succinoylavidin is a chemically modified avidin that has a lower isoelectric point than does avidin itself. It is thus less likely to cause problems with non-specific binding.

Lichstein et al. [Biochemical and Biophysical Research Communications 20(1): 41–45 (1965)] disclose the use of avidin and streptavidin for the characterization of analogs of biotin. Streptavidin, unlike avidin, was determined to be unable to bind the biotin analog dethiobiotin.

Finn et al. [Biochemistry, 23:2554–2558, (1984)] disclose a series of biotinylated and dethiobiotinylated insulins capable of forming complexes with succinoylavidins, in which the distance between the biotin carboxyl group and the insulin varies from 7–20 atoms. In contrast, Finn et al. further disclose the failure of dethiobiotin and its amide to bind to streptavidin, confirming the finding by Lichstein et al.

Ikariyama et al. [Analytical Chem. Symp. Series, 17 (Chem. Sensors): 693–698 (1983)] disclose a bioaffinity sensor for biotin which utilizes a membrane-bound azo dye-enzyme labeled avidin complex. Upon exposure to a solution containing biotin, the enzyme-labeled avidin is released from the membrane to form a stable avidin-biotin complex in solution.

There is a need for a specific binding assay which utilizes a releasable ligand, in a reversible binding displacement system in which a releasable ligand is rapidly displaced by a displacer ligand such that part of an immobilized complex which includes a reporter or an analytically detectable group or, at a minimum, the reporter or analytically detectable group itself, is released into a free liquid medium, and subsequently quantitatively measured. Further, there is a need for a specific binding assay which reduces or eliminates interference that may arise from non-specific binding of the reporter component to an insoluble phase.

SUMMARY OF THE INVENTION

A first assay of this invention is a non-competitive specific binding assay for an analyte comprising the steps of:

A. preparing an immobilized sandwich structure consisting essentially of:

1. a solid support having a first binding partner attached thereto through a linker wherein the first binding partner is selected from the group consisting of streptavidin, avidin, succinylated avidin, nucleic acid and antibody;
2. an analyte or a second binding partner:analyte complex; and
3. a releasable ligand, wherein said releasable ligand is attached:
   a. through a temporary bond to the first binding partner and through a covalent bond to the second binding partner of the second binding partner:analyte complex, wherein the analyte of the second binding partner:analyte complex is attached to a third binding partner having detectable reporter thereon; or
   b. through a temporary bond to a third binding partner having detectable reporter thereon and through a covalent bond to the second binding partner of the second binding partner:analyte complex; or
   c. through a temporary bond to a second binding partner having detectable reporter thereon and through a covalent bond to the analyte;

by contacting said solid support having a first binding partner attached thereto with:
1. liquid sample suspected of containing the analyte;
2. releasable ligand either alone or attached through a covalent bond to the second binding partner; and
3. the second or third binding partner having detectable reporter thereon;

B. separating the immobilized sandwich structure from soluble components;
C. breaking the temporary bond by:
   1. adding an excess of a displacer ligand relative to the releasable ligand; or
   2. adding a displacer ligand wherein the affinity of the displacer ligand to either the first, second or third binding partner is greater than the affinity of the releasable ligand to the first, second or third binding partner; and
D. measuring the detectable reporter in solution.

A second assay of this invention is a competitive specific binding assay for an analyte comprising the steps of:

A. immobilizing on a solid support an analyte or a first binding partner capable of having a releasable ligand attached through a temporary bond;
B. forming an immobilized reporter-labeled complex by contacting the product of step A with a mixture containing reporter-labeled complex prepared by combining:
   1. a liquid sample containing the analyte;
   2. a known quantity of a first binding partner attached through a covalent bond to a releasable ligand, said first binding partner being capable of binding to the analyte, or a known quantity of a releasable ligand:analyte complex wherein the releasable ligand is capable of being attached through a temporary bond to the first binding partner on the solid support; and
   3. a second binding partner having detectable reporter thereon, wherein said second binding partner is capable of being attached through a temporary bond to the releasable ligand or a known quantity of a second binding partner capable of binding with the analyte having detectable reporter thereon;

C. separating the immobilized reporter-labeled complex from soluble components;

D. breaking the temporary bond by:
  1. adding an excess of a displacer ligand relative to the releasable ligand; or
  2. adding a displacer ligand wherein the affinity of the displacer ligand to either the first or second binding partner is greater than the affinity of the releasable ligand to the first or second binding partner; and E. measuring the reporter in solution.

DESCRIPTION OF THE INVENTION

The present invention relates to a specific binding assay which utilizes a non-immune, reversible binding displacement system in which a releasable ligand, a binding partner for the releasable ligand, an analyte of interest, a reporter group, and at least one binding partner for the analyte, are attached to an insoluble phase so as to form reporter-labeled complex bound to an insoluble phase. Preparation of the bound complex is followed by the addition of a displacer ligand which displaces the releasable ligand along with some portion of the reporter-labeled complex, so that the reporter is analytically detectable in a free liquid medium and can be related to the concentration of analyte in the sample.

The releasable ligand is any substance capable of being displaced by a displacer ligand through the addition of an excess of displacer ligand to an insoluble phase having attached to it a releasable ligand, through the use of displacer ligand having an affinity for a binding partner greater than that of the releasable ligand for the binding partner, or through some combination of both. The releasable ligand can be structurally identical to the displacer ligand; such that an excess of displacer ligand is sufficient to displace the releasable ligand; the releasable ligand can be a structural analogue of the displacer ligand; or the releasable ligand can be structurally dissimilar from the displacer ligand.

The non-immune reversible system of this invention, which utilizes a releasable ligand and a displacer ligand to release at least a portion of a reporter-labeled complex from an insoluble phase for determination of an analyte of interest in a free liquid medium, can be applied to any specific binding assay, including competitive and non-competitive immunoassays and DNA probe assays.

The preferred embodiment of the present invention is a non-competitive sandwich immunoassay which utilizes a solid phase onto which is immobilized a first binding partner capable of binding to the analyte of interest, a second binding partner covalently bound to dethiobiotin (DTB), where DTB serves as a releasable ligand, reporter-labeled streptavidin, where the streptavidin serves as a third binding partner and is capable of binding through a temporary bond to the releasable ligand. Biotin serves as the displacer ligand. Alternatively, streptavidin can be covalently bound to the second binding partner and bound to reporter-labeled DTB through a temporary bond. Table 1, sandwich structure 1 represents this preferred embodiment.

The attachment of a binding partner to an insoluble phase can be prepared using known methods such as those disclosed in U.S. Pat. No. 4,661,408, issued to Lau et al. on Apr. 28, 1987. A binding partner for the releasable ligand or a binding partner for the analyte can be attached to a solid carrier by crosslinking, by non-covalent binding, or, preferably by covalent binding. Any solid carrier onto which a specific binding partner can be attached can be used; for example, solid carriers can include, but are not limited to, chromium dioxide particles, silica, iron-oxide, sepharose-based resin columns, polystyrene, polyacrylamide, nylon, cross-linked dextran of nitrocellulose paper, glass beads, phosphor particles, fiber glass, plastic tubes or microtitre plates. Chromium dioxide particles are preferred.

A binding partner for an analyte can be any substance capable of being covalently attached to a solid support or covalently bound to a releasable ligand, displacer ligand, or another binding partner, while maintaining its ability to specifically bind the analyte of interest or the releasable ligand. Examples of binding partners for an analyte include antibodies, antigens, receptors, and nucleic acids.

A binding partner for the releasable ligand can be any substance capable of reversibly binding to the releasable ligand and to the displacer ligand so that a temporary bond is formed. A temporary bond is a bond between a releasable ligand and a binding partner which can be broken upon the addition of a displacer ligand which displaces the releasable ligand. Examples of suitable binding partners for the releasable ligand include avidin, streptavidin, succinylated avidin, biotin, dethiobiotin, iminobiotin, and a functionalized azo dye. Streptavidin is preferred.

A displacer ligand can be any substance capable of displacing a releasable ligand reversibly bound to a binding partner for the releasable ligand through a temporary bond. Examples of suitable displacer ligands include biotin, dethiobiotin, streptavidin, or avidin. Biotin is a preferred displacer ligand.

A releasable ligand is any substance capable of being displaced by a displacer ligand. By displacement is meant the breaking of a temporary bond between the releasable ligand and a binding partner for the releasable ligand upon the addition of a displacer ligand. The releasable ligand can be structurally identical to the displacer ligand; the releasable ligand can be a structural analogue of the displacer ligand; or the releasable ligand can be structurally dissimilar from the displacer ligand. Examples of suitable releasable ligands include dethiobiotin, iminobiotin, 2-[4 (hydroxy-1-naphthalenyl)azo]benzoic acid (NABA), 2-[(8-hydroxy-5-quinolinyl)azo]benzoic acid (QABA), 2-[(2,6-dimethyl-4-hydroxyphenyl)azo] benzoic acid (Dimethyl HABA), streptavidin, succinylated avidin, and avidin. Dethiobiotin is preferred. It is preferable that the affinity of the releasable ligand for the binding partner be greater than $10^7 M^{-1}$.

The displacement of the releasable ligand by the displacer ligand can be achieved through several means. Where the releasable ligand and the displacer ligand are structurally identical, an excess of displacer ligand relative to releasable ligand can be added to break the temporary bond between the releasable ligand and its binding partner. For example, when the releasable ligand is biotin bound through a temporary bond to a binding partner such as a protein, an excess of free biotin relative to the biotin bound to the protein can be added as a displacer ligand to break the temporary bond. The displacement of the releasable ligand can also be achieved by adding a displacer ligand which has a higher affinity constant for the binding partner for the releasable ligand than does the releasable ligand. For example, where the releasable ligand is dethiobiotin and the binding partner is streptavidin, biotin, which has a higher affinity constant for streptavidin than does dethiobiotin, can be used as the displacer ligand. A combination of the two above-described methods for displacing the releasable ligand can also be used.

It is contemplated that other releasable ligands, displacer ligands, and binding partners for the releasable ligands, may be suitable for use with this invention, provided the conditions specified above are met.

The methods of this invention can be practiced using various competitive and noncompetitive specific binding assays. The following examples illustrate several variations of noncompetitive specific binding assays which can be practiced using the method of this invention.

A first example is a specific binding assay determining an analyte in a liquid which comprises:
  (a) providing an insoluble phase having attached to it a first binding partner capable of binding to the analyte;
  (b) contacting the insoluble phase with the following components:
    1. liquid medium suspected of containing the analyte;
    2. a second binding partner, which is capable of binding to the analyte, covalently bound to a releasable ligand;
    3. a third binding partner which is capable of binding to the releasable ligand and which has a detectable reporter thereon;
  to form an immobilized sandwich structure, such that the releasable ligand is attached through a temporary bond to the third binding partner;
  (c) separating unreacted components from the immobilized sandwich structure;
  (d) contacting the immobilized sandwich structure with a displacer ligand so that the temporary bond between the releasable ligand and the third binding between the releasable ligand and the third binding partner for the releasable ligand is broken and a portion of the sandwich structure containing the reporter is released from the immobilized sandwich structure; and
  (e) measuring the released reporter in free solution.

Table 1, sandwich structure 1 depicts several combinations of releasable ligand, displacer ligand, and binding partner for the releasable ligand which are suitable for use in the first example of a specific binding assay which uses the method of this invention. In a preferred embodiment, the first two components, comprising the liquid medium suspected of containing the analyte and the second binding partner, which is capable of binding to the analyte, covalently bound to a releasable ligand, are first contacted with the insoluble phase having attached to it a first binding partner capable of binding to the analyte. This step is followed by washing to remove unreacted components, and the wash step is followed by contact with the third component, comprising a third binding partner capable of binding to the releasable ligand and having attached to it a detectable reporter.

The first binding partner for the releasable ligand can be covalently attached directly to the insoluble phase using known linking compounds or can be attached using binding partners, such as biotin, which can, in turn, be covalently attached to the insoluble phase.

A second example is a specific binding assay for determining an analyte in a liquid medium which comprises:
  (a) providing an insoluble phase having attached to it a first binding partner capable of binding to a releasable ligand;
  (b) contacting the insoluble phase with the following components:
    1. a liquid medium suspected of containing the analyte;
    2. a second binding partner which is covalently bound to a releasable ligand and which is capable of binding to the analyte; and
    3. a third binding partner capable of binding to the analyte and having a detectable reporter thereon;
  to form an immobilized reporter-labeled sandwich structure in which the releasable ligand is bound through a temporary bond to the first binding partner;
  (c) separating unreacted components from the immobilized reporter-labeled sandwich structure;
  (d) contacting the immobilized reporter-labeled sandwich structure with a displacer ligand so that the temporary bond between the releasable ligand and the first binding partner for the releasable ligand is broken and a portion of the sandwich structure containing the reporter is released; and
  (e) measuring the released reporter in free solution.

Table 1, sandwich structure 2 depicts several combinations of releasable ligand, displacer ligand, and binding partner for the releasable ligand which are suitable for use in the second example of a specific binding assay which uses the method of this invention.

A third example is a specific binding assay tot determining an analyte in a liquid medium which comprises:
  (a) providing an insoluble phase having attached to it a first binding partner capable of binding to an analyte;
  (b) contacting the insoluble phase having attached to it a first binding partner capable of binding to an analyte with:
    1. a liquid medium suspected of containing the analyte;
    2. a releasable ligand which has been activated so that it is capable of covalently binding to the analyte;
  to form an immobilized sandwich structure in which the releasable ligand is covalently bound to the analyte;
  (c) separating unreacted components from the immobilized sandwich structure;
  (d) contacting the immobilized sandwich structure with a second binding partner capable of binding to the releasable ligand and having a detectable reporter thereon;
  to form an immobilized reporter-labeled sandwich structure;
  (e) contacting the immobilized reporter-labeled sandwich structure with a displacer ligand so that the temporary bond between the releasable ligand and the second binding partner for the releasable ligand is broken and a portion of the sandwich structure containing the reporter is released; and
  (f) measuring the released reporter in free solution.

The releasable ligand can be reacted with the liquid medium suspected of containing the analyte so as to covalently bind the releasable ligand to the analyte prior to, or simultaneously with, contact with the insoluble phase. It is preferable to react the analyte with the releasable ligand prior to contact with the insoluble phase. The releasable ligand can be activated to enable a covalent bond to be formed between the releasable ligand and the analyte. Activation of the releasable ligand can be accomplished by using known methods for preparing biotinylated analytes, such as Ishikawa et al., *Clinic Biochem*, 23:445-453 (1990).

Table 1, sandwich structure 3 depicts several combinations of releasable ligand, displacer ligand, and binding partner for the releasable ligand which are suitable for use in the third example of a specific binding assay which uses the method of this invention.

A fourth example is a specific binding assay for determining an analyte in a liquid medium which comprises:
(a) providing an insoluble phase having attached to it a first binding partner capable of binding to an analyte;
(b) incubating the following components:
1. a liquid medium suspected of containing the analyte;
2. a second binding partner which is capable of binding to the analyte and which is covalently bound to a first releasable ligand;
3. a third binding partner capable of binding to the first releasable ligand; and
4. a second releasable ligand capable of binding to the third binding partner and having a detectable reporter thereon;
to form a mixture containing a reporter-labeled complex;
(c) contacting the insoluble phase with the mixture containing the reporter-labeled complex to form an immobilized reporter-labeled sandwich structure;
(d) contacting the immobilized reporter-labeled sandwich structure with a displacer ligand so that the temporary bonds between the first and second releasable ligand and the third binding partner are broken and a portion of the complex containing the reporter is released; and
(e) measuring the released reporter in free solution.

Table 1, sandwich structure 4 depicts several combinations of releasable ligand, displacer ligand, and binding partner for the releasable ligand which are suitable for use in the fourth example of a specific binding assay which uses the method of this invention.

For the above-mentioned examples, the insoluble phase can be contacted simultaneously with all of the components specified, followed by washing to remove unreacted components, or with the components added sequentially in the order indicated with washing after contact with each component, or with the components added in any other desired sequence. In the preferred embodiment (FIG. 1, sandwich structure 1), it is preferred that the components are added sequentially as described above. Further, for all of the above mentioned examples, the releasable ligand can be structurally identical to the displacer ligand, an analogue of the displacer ligand, or structurally dissimilar from the displacer ligand. If the releasable ligand is structurally identical to the displacer ligand, the displacer ligand must be present in excess of the releasable ligand in order to successfully displace it.

TABLE 1

IMMOBILIZED SANDWICH STRUCTURES AND DISPLACER LIGANDS-NONCOMPETITIVE SPECIFIC BINDING ASSAYS

SANDWICH STRUCTURE 1

TABLE 1-continued

IMMOBILIZED SANDWICH STRUCTURES AND DISPLACER LIGANDS-NONCOMPETITIVE SPECIFIC BINDING ASSAYS

INSOLUBLE PHASE-BP1:ANALYTE:BP2—RL~BP3—*

| | |
|---|---|
| Third Binding Partner (BP3) = | Streptavidin, succinylated avidin and avidin where the releasable ligand is biotin, dethiobiotin, iminobiotin, and functionalized azo dye; biotin, dethiobiotin, iminobiotin, and a functionalized azo dye where the releasable ligand is streptavidin, succinylated avidin, or avidin |
| Releasable Ligand (RL) = | Biotin, dethiobiotin, iminobiotin, functionalized azo dye, streptavidin, succinylated avidin and avidin |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| First Binding Partner (BP1) = | Any specific binding partner for the analyte, including antibodies, antigens, nucleic acids, and receptors |
| Second Binding Partner (BP2) = | Any specific binding partner for the analyte, including antibodies, antigens, nucleic acids, and receptors |

* = detectable reporter group
~ = temporary bond
: = bond between binding partner for the analyte and the analyte
— = covalent bond

SANDWICH STRUCTURE 2
INSOLUBLE PHASE-BP1~RL—BP2:ANALYTE:BP3—*

| | |
|---|---|
| First Binding Partner (BP1) = | Streptavidin, succinylated avidin, and avidin. |
| Releasable Ligand (RL) = | Biotin, dethiobiotin, iminobiotin, and functionalized azo dye |
| Displacer Ligand (DL) = | Biotin, dethiobiotin (can be used to displace releasable ligands having lower affinity for the binding partner for the releasable ligand, such as iminobiotin or functionalized azo dye, or can displace dethiobiotin contained in complex if excess of free dethiobiotin added), and streptavidin (can displace streptavidin in complex if excess free streptavidin added) |
| Second Binding Partner (BP2) = | Any specific binding partner for the analyte, including antibodies, antigens, nucleic acids, and receptors |
| Third Binding Partner (BP3) = | Any specific binding partner for the analyte, including antibodies, antigens, nucleic acids, and receptors |

* = detectable reporter group
~ = temporary bond
: = bond between binding partner for the analyte and the analyte
— = covalent bond

SANDWICH STRUCTURE 3
INSOLUBLE PHASE-BP1:ANALYTE—RL~BP2—*

| | |
|---|---|
| Second Binding | Streptavidin, succinylated |

TABLE 1-continued
IMMOBILIZED SANDWICH STRUCTURES AND DISPLACER LIGANDS-NONCOMPETITIVE SPECIFIC BINDING ASSAYS

| | |
|---|---|
| Partner (BP2) = | avidin, and avidin |
| Releasable Ligand (RL) = | Biotin, dethiobiotin, iminobiotin, and functionalized azo dye |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| First Binding Partner (BP1) = | Any specific binding partner for the analyte, including antibodies, antigens, nucleic acids, and receptors |

\* = detectable reporter group
~ = temporary bond
: = bond between binding partner for the analyte and the analyte
— = covalent bond

SANDWICH STRUCTURE 4
INSOLUBLE PHASE-BP1:ANALYTE:BP2—RL~BP3~RL—\*

| | |
|---|---|
| Third Binding Partner (BP3) = | Streptavidin, succinylated avidin, and avidin |
| Releasable Ligand (RL) = | Biotin, dethiobiotin, iminobiotin, and functionalized azo dye |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| First Binding Partner (BP1) = | Any specific binding partner for the analyte, including antibodies, antigens, nucleic acids, and receptors |
| Second Binding Partner (BP2) = | Any specific binding partner for the analyte, including antibodies, antigens, nucleic acids, and receptors |

\* = detectable reporter group
~ = temporary bond
: = bond between binding partner for the analyte and the analyte
— = covalent bond The following are examples of competitive specific binding assays which may be practiced using the method of this invention.

A fifth example of a specific binding assay for determining an analyte in a liquid medium comprises:
(a) providing an insoluble phase having an analyte of interest attached thereto;
(b) forming a mixture of reporter-labeled complex by combining the following components:
 1. a measured amount of liquid medium suspected of containing the analyte;
 2. a known quantity of a first binding partner which is capable of binding to the analyte and which is covalently bound to a releasable ligand;
 3. a second binding partner capable of binding to the releasable ligand and having a detectable reporter thereon;
(c) contacting the mixture containing the reporter-labeled complex with the insoluble phase to form an immobilized reporter-labeled complex;
(d) separating the immobilized reporter-labeled complex from soluble components;
(e) contacting the immobilized reporter-labeled complex with a displacer ligand so that a temporary bond between the releasable ligand and the second binding partner for the releasable ligand is broken and a portion of the complex containing the reporter is released; and
(f) measuring the released reporter in free solution.

Table 2, structure 1 depicts several combinations of releasable ligand, displacer ligand, and binding partner for the releasable ligand which are suitable for use in the fifth example of a specific binding assay which uses the method of this invention.

A sixth example of a specific binding assay for determining an analyte in a liquid medium comprises:
(a) providing an insoluble phase having an analyte of interest attached thereto;
(b) forming a mixture of a reporter-labeled complex by combining the following components:
 1. a measured amount of liquid medium suspected of containing the analyte;
 2. a known quantity of a first binding partner which is capable of binding to the analyte and which is covalently bound to a second binding partner capable of binding to a releasable ligand; and
 3. a releasable ligand having a detectable reporter thereon;
(c) contacting the insoluble phase with the mixture of reporter labeled complex to form an immobilized reporter-labeled complex;
(d) separating the immobilized reporter-labeled complex from soluble components;
(e) contacting the immobilized reporter-labeled complex with a displacer ligand so that a temporary bond between the releasable ligand and the second binding partner for the releasable ligand is broken and a portion of the complex containing the reporter is released; and
(f) measuring the released reporter in free solution.

Table 2, structure 2 depicts several combinations of releasable ligand, displacer ligand, and binding partner for the releasable ligand which are suitable for use in the sixth example of a specific binding assay which uses the method of this invention.

A seventh example of a specific binding assay for determining an analyte in a liquid medium comprises:
(a) providing an insoluble phase having a first binding partner capable of binding to a releasable ligand attached thereto;
(b) forming a mixture of a reporter-labeled complex by combining the following components:
 1. a measured amount of liquid medium suspected of containing the analyte;
 2. a known quantity of a releasable ligand covalently bound to the analyte; and
 3. a known quantity of a second binding partner capable of binding to the analyte and having a detectable reporter thereon;
(c) contacting the mixture containing the reporter-labeled complex with the insoluble phase to form an immobilized reporter-labeled complex;

(d) separating the immobilized reporter-labeled complex from soluble components;

(e) contacting the immobilized reporter-labeled complex with a displacer ligand so that a temporary bond between the releasable ligand and the first binding partner for the releasable ligand is broken and a portion of the complex containing the reporter is released; and (f) measuring the released reporter in free solution.

Table 2, structure 3 depicts several combinations of releasable ligand, displacer ligand, and binding partner for the releasable ligand which are suitable for use in the seventh example of a specific binding assay which uses the method of this invention.

TABLE 2

IMMOBILIZED STRUCTURES AND DISPLACER LIGANDS-COMPETITIVE SPECIFIC BINDING ASSAYS

STRUCTURE 1
INSOLUBLE PHASE ANALYTE:BP1—RL~BPS—*

| | |
|---|---|
| Second Binding Partner (BP2) = | Streptavidin, succinylated avidin, and avidin |
| Releasable Ligand (RL) = | Biotin, dethiobiotin, and iminobiotin, functionalized azo dye |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| First Binding Partner (BP1) = | Any specific binding partner for the analyte, including antibodies, antigens, nucleic acids, and receptors |

* = detectable reporter group
~ = temporary bond
: = bond between binding partner for the analyte and the analyte
— = covalent bond

STRUCTURE 2
INSOLUBLE PHASE-ANALYTE:BP1—BP2~RL—*

| | |
|---|---|
| Second Binding Partner (BP2) = | Streptavidin, succinylated avidin, and avidin |
| Releasable Ligand (RL) = | Biotin, dethiobiotin, iminobiotin, and functionalized azo dye |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| First Binding Partner (BP1) = | Any specific binding partner for the analyte, including antibodies, antigens, nucleic acids, and receptors |

* = detectable reporter group
~ = temporary bond
: = bond between binding partner for the analyte and the analyte
— = covalent bond

STRUCTURE 3

TABLE 2-continued

IMMOBILIZED STRUCTURES AND DISPLACER LIGANDS-COMPETITIVE SPECIFIC BINDING ASSAYS

INSOLUBLE PHASE-BP1~RL—ANALYTE:BP2—*

| | |
|---|---|
| First Binding Partner (BP1) = | Streptavidin, succinylated avidin, and avidin |
| Releasable Ligand (RL) = | Biotin, dethiobiotin, iminobiotin, and functionalized azo dye |
| Displacer Ligand (DL) = | Biotin, dethiobiotin (can be used to displace releasable ligands having lower affinity for the binding partner of the releasable ligand, such as iminobiotin or functionalized azo dye, or can displace dethiobiotin contained in complex if excess of free dethiobiotin added), and streptavidin (can displace streptavidin in complex if excess free streptavidin added) |
| Second Binding Partner (BP2) = | Any specific binding partner for the analyte, including antibodies, antigens, nucleic acids, and receptors |

* = detectable reporter group
~ = temporary bond
: = bond between binding partner for the analyte and the analyte
— = covalent bond The affinity of the displacer ligand for the binding partner must be greater than the affinity of the releasable ligand to the binding partner whenever the displacer ligand is structurally dissimilar to the releasable ligand. Preferably, the ratio of the affinity of the displacer ligand for the binding partner to the affinity of the releasable ligand to the binding partner is $10^2$.

Any reporter group which is analytically detectable upon release of the reporter-labeled portion of the complex into free solution as a result of the displacement of the releasable ligand by the displacer ligand can be used. Examples of such reporter groups include but are not limited to: enzymes, fluorescent dyes, phosphorescent dyes, radioisotopes, and electron-dense markers. Enzymes are preferred reporters. The reporter group can be attached to any portion of the complex which is ultimately released into free solution, depending upon the particular assay configuration employed. For example, the reporter group can be attached to the releasable ligand, to the binding partner for the releasable ligand or the binding partner for the analyte. The reporter group can be attached using known methods [Kitagawa, Enzyme Immunoassays, pp. 81-89, Igaku-Shoah, Tokyo, N.Y. (1981)].

In accordance with those examples of this invention described above which refer specifically to specific binding assays in which an insoluble phase has attached to it a binding partner, the preferred releasable ligand is dethiobiotin. It is especially preferred that dethiobiotin be attached through a hydrophilic spacer molecule to a binding partner. The releasable ligand can be conjugated to the carrier via a hydrophilic spacer, derived from a very water-soluble compound functionalized on one end with an amine group and on the other end with a carboxyl group and thus properly designed as an alpha, omega-amino acid.

The preferred spacer molecules useful in this invention are of the general formula:

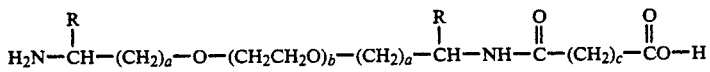

where
R=H or CH$_3$
a=1 or 2
b=1-10
c=2-4

The hydrophilic spacer molecule of the following formula (AA-16) is especially preferred:

Compounds of this class can be synthesized by reacting one mole of an appropriate diamine, such as a bis-(aminoalkyl) ether of ethylene glycol, diethylene glycol, triethylene glycol, and polyethylene glycol, with one mole of a cyclic dicarboxylic acid anhydride, such as succinic anhydride, glutaric anhydride, and adipic anhydride. It is advantageous to use an organic solvent system in which both the diamine and the anhydride are soluble but in which the desired reaction product is insoluble. In general, acetonitrile, tetrahydrofuran, diethyl ether and mixtures thereof are suitable.

It is anticipated that other hydrophilic spacers derived from water-soluble alpha, omega-amino acids can be useful in this invention, including but not limited to those of the general formula

where n=2-6. Such compounds are commercially available.

We estimate that free (unconjugated) dethiobiotin binds to streptavidin with a binding constant of about $10^{11}$ M$^{-1}$. This is a rather large binding constant and any feature that increases or, alternatively, decreases the rate at which a dethiobiotin-streptavidin complex dissociates will decrease the rate with which a dethiobiotin conjugate complex can be released from streptavidin bound to a solid phase by addition of free biotin. Rapid release of dethiobiotin conjugate complexes is an essential feature of our invention.

Garlick et al. [J. Biol. Chem. 263: 210-215 (1988)] have shown that conjugation of biotin and biotin analogs directly to hydrophobic moieties decreases the rate of dissociation of the conjugate from avidin. Use of a hydrophilic linker provides a means for avoiding the hydrophobic effect and insuring an adequate rate of release of dethiobiotin-labeled complexes from streptavidin.

EXAMPLE 1

Determination Of TSH By Measurement Of An Enzyme-Labeled Complex Released From A Solid Support In A Noncompetitive Immunoassay Using Dethiobiotin As A Releasable Ligand And Biotin As A Displacer Ligand 1. Synthesis of anti-TSH antibody covalently bound to dethiobiotin (DTB; anti-TSH IgG1-DTB)

This example illustrates the use and effect of a hydrophilic spacer inserted between DTB, which can act as a releasable ligand, and anti-TSH IgG1 antibody used as a binding partner for the analyte, on the attachment of the DTB-AA-16-anti-TSH IgG1 complex to enzyme-labeled streptavidin.

A vial containing 51.00 mg of disuccinimidyl carbonate (DSC; Aldrich Co.) and enough dry dimethyl sulfoxide (DMSO; Aldrich Co.) to give a total weight of 3.400 grams was agitated to dissolve the DSC. The density was determined to be 1.104 by weighing a sample of known volume. The concentration of DSC was calculated as follows:

Concentration of DSC=(51.00 mg×1.104)(256.2×3400 mg)=6.693×10$^{-5}$ (mmoles/μL)

A vial containing 12.50 mg (5.834×10$^{-5}$ moles) of dethiobiotin (DTB; Sigma Co.) and 995 μL DSC stock solution (5.647×10$^{-5}$ moles of DSC) was agitated to dissolve the DTB. Twenty microliters of triethylamine (TEA; Aldrich Co.), was added and the mixture was agitated at room temperature for an hour. The concentration of the resulting solution, hereinafter referred to as activated DTB solution, was calculated as follows:

Concentration of activated DTB=(12.50 mg×1.104)/(214.3×995 μL)=6.472×10$^{-5}$ (mmole/μL)

Anti-TSH IgG1 monoclonal antibody was produced using known methods from hybridoma cell line 4/46.2.2.1 obtained from the E. I. du Pont de Nemours and Co. IgG1 was isolated from ascites fluid derived from the above cell line by affinity chromatography using a Protein-A-Sepharose CL 4B column (Pharmacia Co.). The IgG was eluted from the column using a sodium acetate buffer, pH 5.0, and then dialyzed against 0.2M sodium phosphate buffer, pH 7.4 overnight in a cold room at 4°-8° C. A 2 mL portion of this solution, containing 2.64 mg/mL anti-TSH IgG1 antibody, was mixed with a 20-fold molar excess of activated DTB in dimethyl sulfoxide. The reaction mixture was allowed to rock gently at room temperature for a period of 60 minutes, loaded onto a Sephadex G-25 column (1.0×30 cm; Pharmacia Co.), and the anti-TSH IgG1 antibody-DTB eluted with 0.2M sodium phosphate buffer, pH 7.0. The fractions of anti-TSH IgG1 antibody-DTB were collected and pooled.

2. Synthesis of anti-TSH IgG2-β-Galactosidase

Anti-TSH IgG2 monoclonal antibody was produced from cell line 972.3 obtained from the Hybritech Co. The isolation process was the same as described above for the isolation of the anti-TSH IgG1 antibody. Six milliliters of a solution containing 11.2 mg/mL anti-TSH IgG2 was dialyzed against phosphate buffer saline, pH 7.4, overnight in at 4°-8° C. The concentration of the anti-TSH IgG2 solution was adjusted to 5 mg/mL with phosphate saline solution and a solution containing 68.4 mg anti-TSH IgG2 was combined with a 30 fold-molar excess of N-succinimidyl-4-(N-maleimidomethyl)cyclohexane-1-carboxylate (SMCC; Pierce Chemical Co.) in dimethyl sulfoxide (DMSO; Pierce Chemical Co.) and gently agitated at room temperature for 30 minutes. The solution was then loaded onto a Sephadex G-25 column (1.0×30 cm; Pharmacia Co.) and the anti-TSH IgG2 eluted with phosphate saline buffer, pH 6.5. The resulting fractions of maleimido-activated anti-TSH IgG2 were collected and pooled.

A total of 401 mg of $\beta$-galactosidase (Boehringer-Mannheim Biochemicals; 22.4% by weight protein) was reconstituted with 88 mL of phosphate saline buffer, pH 6.5. The maleimido-activated anti-TSH IgG2 was then combined with thiol containing $\beta$-galactosidase) in a 3 to 1 molar ratio (3 moles antibody and 1 mole $\beta$-galactosidase) and the reaction was allowed to proceed for 60 minutes at room temperature. The reaction was then quenched by the addition of 1 mM of N-ethylmaleimide (NEM; Sigma Chemical Co.) and incubated for 30 minutes at room temperature. The resulting crude anti-TSH IgG2-$\beta$-galactosidase was isolated by HPLC using a GF-450XL size exclusion column (22.5 mm×25 cm; Rockland Co.), and then eluted with 0.2M sodium phosphate solution containing 0.1% sodium azide buffer, pH 7.0, at a flow rate of 2 mL/minute. The fractions of anti-TSH IgG2-$\beta$-galactosidase exhibiting both immunoactivity and enzymatic activity (as determined using known methods such as radioimmunoassay, RIA and enzyme activity determination) were collected and pooled.

3. Quantitative Thyroid Stimulating Hormone (TSH) Immunoassay

A set of test tubes containing 650 $\mu$g of streptavidin-immobilized chromium dioxide particles and 20 $\mu$g of anti-TSH IgG1-DTB were incubated at 37° C. for 15 minutes. The streptavidin had been previously immobilized onto chromium dioxide magnetic particles using a known method, such as that disclosed in U.S. Pat. No. 4,661,408. Following incubation, the particles were washed by adding 500 $\mu$L of Hepes buffer, pH 7.5, to each test tube. The test tubes containing anti-TSH IgG1-DTB-streptavidin-chromium dioxide particles were then divided into two concentration series; 500 $\mu$L TSH analyte at a concentration of 0 $\mu$IU/mL was added to each tube of one set, and 500 $\mu$L of TSH at a concentration 55 $\mu$IU/mL (E. I. du Pont de Nemours and Co. ) was added to each tube of the other set. Both sets were incubated at 37° C. for 10 minutes and washed three times with 500 $\mu$L of Hepes buffer. Following this, 500 $\mu$L of anti-TSH IgG2-$\beta$-galactosidase was added to all of the tubes, the mixtures was incubated at 37° C. for 10 minutes, and the particles washed four times with 500 $\mu$L of Hepes buffer, pH 7.5.

The test tubes were then divided into two sets, each set including tubes containing TSH at both 0 and 55 $\mu$IU/mL concentration levels. Into the first set of test tubes (hereinafter referred to as SET A1), was added 250 $\mu$L of Hepes buffer and 250 $\mu$L of chlorophenol red $\beta$-D-galactopyranoside (CPRG; Boehringer-Mannheim Biochemical) substrate. The reaction was allowed to proceed at 37° C. for 30 minutes and was then quenched b the addition of 5 mg of o-nitrophenyl-$\beta$-D-galactopyranoside (ONPG; Boehringer-Mannheim Biochemical). The absorption of the colored product, based on measurement of the enzyme-labeled complex while still bound to the solid phase, was measured at 577 nm using an aca ® discrete clinical analyzer (E. I. du Pont de Nemours and Co.).

Into the second set of test tubes (hereinafter referred to as SET B1-1 ), was added 300 $\mu$L of 0.68 mg/mL biotin (Sigma Chemical Co. ) as a displacer ligand to displace the dethiobiotin and release the enzyme-labeled complex. The test tubes were incubated at 37° C. for 10 minutes and 250 $\mu$L of the supernatant of each test tube was then removed and placed in a clean test tube. Into these test tubes, containing released enzyme-labeled complex (hereinafter referred to as SET B1-2), was added 250 $\mu$L of CPRG. After incubation for 30 minutes at 37° C., the reaction was quenched by the addition of 5 mg of ONPG and the absorption of the colored product was monitored at 577 nm with an aca ® discrete clinical analyzer (E. I. du Pont de Nemours and Co.).

The steps as described above for the measurement of the enzyme-labeled released complex were repeated (hereinafter referred to as SET B1-3). Samples of CPRG and anti-TSH IgG1-DTB were measured at 577 nm with an aca ® discrete clinical analyzer as negative controls. Table 1 depicts the measured absorption at 0 $\mu$IU/mL and 55 $\mu$IU/mL TSH for the bound and released enzyme-labeled complexes.

TABLE 3

| Sample | TSH Concentration ($\mu$IU/mL) | |
|---|---|---|
| | 0 (mA) at 577 nm | 55 (mA) at 577 nm |
| Substrate blank | 20.5 | — |
| DTB-IgG1 | 20.4 | — |
| Bound Complex (Set A1) | 44.7 | 1293 |
| Released Complex Set B1-2) | 39.9 | 660.4 |
| Released Complex (Set B1-3) | 26.6 | 179.3 |

EXAMPLE 2

The Effect Of The Presence Of A Hydrophilic Spear In An Enzyme-Labeled Complex On The Attachment Of The Complex To A Reporter-Labeled Binding Partner For A Releasable Ligand This example illustrates the use and effect of a hydrophilic spacer inserted between DTB serving as a releasable ligand, and anti-TSH IgG2 antibody used as a binding partner for the analyte, on the attachment of the DTB-AA-16-anti-TSH IgG2 complex to enzyme-labeled streptavidin. The immobilized reporter-labeled complex formed is chromium dioxide particle-anti-TSH IgG1:TSH:anti-TSH IgG2-AA-16-DTB~streptavidin-alkaline phosphatase.

1. Synthesis of Anti-TSH IgG2-DTB

Anti-TSH IgG2 monoclonal antibody was produced from hybridoma cell line 972.3 obtained from the Hybritech Co. using known methods. Anti-TSH IgG2-DTB was prepared using the procedure described in Example 1.

2. Synthesis of Anti-TSH IgG2-AA-16-DTB

The hydrophilic spacer used was AA-16 of the formula:

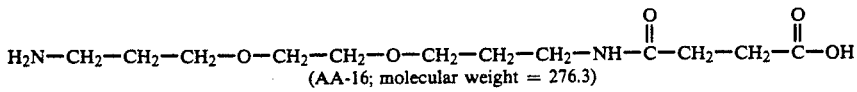
(AA-16; molecular weight = 276.3)

AA-16 was produced by reacting one mole of succinic anhydride with one mole of ethylene glycol bis(3-aminopropyl) ether, (American Tokyo Kasei, Inc). The reaction was carried out using acetonitrile as a solvent because both reactants are very soluble in acetonitrile, while AA-16 is very insoluble in acetonitrile.

A weight of 50.03 grams (0.284 mole) of ethylene glycol his (3-aminopropyl) ether and 200 mL of acetonitrile was added to a 1-liter, round-bottom flask equipped with a mechanical stirrer, dropping funnel, and nitrogen flush. The solution was stirred vigorously and a solution of succinic anhydride (0.284 moles ) (Aldrich Co.) in 200 mL of acetonitrile was added dropwise over a 2 hour period. During this time, AA-16 precipitated out of the reaction solution as a viscous "oil" which partially solidified. When all of the succinic anhydride solution had been added, the acetonitrile was removed by decantation and the residue was washed with three 100-mL portions of fresh acetonitrile. Following this wash, a solution of 400 mL of anhydrous ether was added to the reaction flask and the reaction mixture was subsequently stirred continuously for several hours. The solidified AA-16 was observed to gradually change in consistency to that of a fine power. The reaction mixture was gravity filtered through a fluted filter under a dry nitrogen atmosphere and most of the ether was removed by flushing with dry nitrogen. The resulting AA-16 reaction product was then dried by allowing it to sit in a vacuum desiccator for several hours.

Based on acid and base analytical titrations, the product was determined to have a purity of 95%. AA-16 was determined to be very water-soluble and very hygroscopic, but insoluble in most organic solvents. AA-16 was found to dissolve in warm DMSO containing triethylamine (TEA) (16.5 μL of DMSO plus 0.825 μL of TEA per mg of AA-16).

A vial containing 50.29 mg of disuccinimidyl carbonate (DSC) and 3,358 mg dry DMSO was agitated to dissolve the DSC to a final concentration of DSC of $6.359 \times 10^{-5}$ mmole/μL. A solution of 895 μL DSC solution ($5.69 \times 10^{-5}$ mole) was then combined with 11.08 mg ($5.170 \times 10^{-5}$ mole) DTB and the mixture agitated to dissolve the DTB. Following this, 20 μL TEA was added and the solution agitated gently at room temperature for 60 minutes.

A 500 μL conical Reacti-Vial ® containing 16.54 mg AA-16 ($5.687 \times 10^{-5}$ mole, prepared using the procedure described above), 271 μL dry DMSO, and 13.5 μL TEA was equipped with a conical, magnetic stirrer, tightly capped, and placed in an aluminum heating block maintained at 40°-50° C. and stirred until a free flowing solution was obtained. The solution of AA-16 in DMSO was added to a solution of activated DTB and the Reacti-Vial ® was rinsed three times with 100 μL DMSO. The resulting mixture was allowed to stand at room temperature overnight. Following this, 894 μL of DSC solution ($5.687 \times 10^{-5}$ moles DSC) was mixed gently for at least 60 minutes at room temperature. The density of the resulting solution, hereinafter referred to as activated DTB-AA-16 solution, was then determined by weighing a sample of known volume.

A 2 mL portion of a solution of 5 mg/mL anti-TSH IgG2 antibody in 0.2M sodium phosphate buffer, pH 8.0, derived from Hybritech cell line 972.3 and prepared using the same procedure as described in Example 1, was combined with a 20-fold molar excess of activated DTB-AA-16 solution in DMSO. The reaction mixture was allowed to mix gently at room temperature for about 60 minutes. The resulting solution containing the anti-TSH IgG2-AA-16-DTB complex was loaded onto a Sephadex G-25 column (1.5×30 cm; Pharmacia Co.), and then eluted with 0.2M sodium phosphate buffer, pH 7.0. The resulting fractions containing anti-TSH IgG2-AA-16-DTB were collected and pooled.

Streptavidin-alkaline phosphatase (enzyme-labeled streptavidin) was obtained from the Chemicon Company.

3. Quantitative TSH Immunoassay

Two series of test tubes were prepared; one series containing 500 μL of TSH at a concentration of 0 μIU/mL and the other containing 500 μL of TSH at a concentration of 50 μIU/mL The test tubes were then divided into two sets, each set including tubes containing TSH at both 0 and 55 μIU/mL concentration levels. A solution of 500 μL of 10 μg anti-TSH IgG2-DTB was added to one set of test tubes (hereinafter referred to as Set A2), and a solution of 500 μL of 10 μg anti-TSH IgG2-AA-16-DTB was added to the other set (hereinafter referred to as Set B2). The reaction mixtures in the two sets of test tubes were then treated in the following identical manner. The reaction mixtures were incubated for 10 minutes at 37° C.; 250 μg of chromium dioxide particles onto which anti-TSH IgG1 antibody had been previously immobilized was added; the reaction mixtures were incubated for 10 minutes at 37° C. and subsequently washed with 500 μL of a buffer composed of 250 mM tris, 50 mM sodium borate, pH 7.8. Following this, 500 μL of 0.2 μg of streptavidin-alkaline phosphatase conjugate was added, the reaction mixtures were incubated at 37° C. for 10 minutes, and subsequently washed with 500 μL of 250 mM tris, 50 mM sodium borate, pH 7.8.

Aliquots of 250 μL of biotin solution containing 6.8 mg/mL biotin and 300 μL of fluorometric substrate, 4-methylumbelliferyl phosphate (MUP; Boehringer-Mannheim Biochemical) in 2.5 mM DEA were added to each of the Set A2 and B2 test tubes, the reaction mixtures were incubated at 37° C. for 5 minutes, the reaction was then quenched by the addition of 300 μL 0.5M EDTA solution. The fluorescence intensity of the methylumbelliferone (MU) generated by the bound fraction of the resulting chromium dioxide particle-anti-TSH IgG1:TSH:anti-TSH IgG2-AA-16-DTB~streptavidin-alkaline phosphatase complex was measured using a SLM Aminco fluorometer (SLM Instrument, Inc.).

TABLE 4

Comparison Of The Measurement Of The Bound Complex With And Without A Hydrophilic Spacer

| Sample | Concentration of TSH (μIU/mL) | |
|---|---|---|
| | 0 F.I.U. | 50 F.I.U. |
| A2 (Complex without Hydrophilic Spacer) | 0.66 | 1.03 |
| B2-2 (Complex with Hydrophilic Spacer) | 0.5 | 7.1 |

F.I.U. = Fluorescent Intensity Unit
F.I.U. as determined using SLM Aminco SPF 500C spectrofluorometer (SLM Instrument, Inc.) with the following instrument parameter set up: Ex/Em = 375/475 nm, res Ex/Em = 4/10 nm, Int. time 0.1 sec., Gain = 10, HV = 715 V.

The results shown in Table 2 indicate that for Set A2, the DTB-anti-TSH IgG2 complex without a hydrophilic spacer was able to bind less alkaline phosphatase-labeled streptavidin than did set B2-2, containing the DTB-AA-16-anti-TSH IgG complex. This difference in binding ability may be explained in terms of the effect of steric hindrance.

EXAMPLE 3

Determination Of TSH By The Release and Measurement Of Alkaline Phosphatase-Labeled Streptavidin From A Chromium Dioxide Particle-Anti-TSH IgG1:TSH:Anti-TSH IgG2-AA-16-DTB~Streptavidin-Alkaline Phosphatase Complex Two sets of test tubes were prepared; each tube contained 250 μg chromium dioxide particles onto which had been previously immobilized anti-TSH IgG1; 500 μL of 0.5 μg anti-TSH IgG2-AA-16-DTB, and 500 μL of TSH, where the test tubes of each set contained concentrations of TSH as follows: 0, 0.1, 0.5, 5.0, 25, and 50 μIU/mL. After incubation at 37° C. for 30 minutes, the chromium dioxide particles were washed three times with 500 μL of 250 mM tris, 50 mM sodium borate, pH 7.8 buffer. 500 μL of a solution of 0.5 μg/mL streptavidin-alkaline phosphatase was added to each test tube, the test tubes were incubated at 37° C. for 15 minutes, and the particles were washed four times with 500 μL 250 mM tris, 50 mM sodium bisulfite buffer, pH 7.5. An aliquot of 300 μL of a solution of 6.8 mg/mL biotin was added to each test tube and the tubes were incubated at 37° C. for 10 minutes. The particles were magnetically separated and 250 μL of the supernatant from each test tube was transferred to a clean set of test tubes (hereinafter referred to as set A3). A solution of 2.25 mM MUP in 2.5M DEA buffer which had been pre-heated was added to each test tube and the fluorescence intensities determined by a rate mode using an SLM Aminco photon counter 8000 C Spectrofluorometer (SLM Instrument, Inc.) The results, shown in Table 3, indicate that the method of this invention can be successfully used in a simultaneous assay format to provide a means for the quantitative determination of analytes.

TABLE 5

| Set A3: Simultaneous TSH Assay Format | |
|---|---|
| Concentration of TSH (μIU/mL) | Signal (F.I.U./minute) |
| 0 | 0.657 |
| 0.1 | 0.768 |
| 0.5 | 3.200 |
| 5 | 22.11 |
| 25 | 122.24 |
| 50 | 213.97 |

AMINCO 8000C instrument parameters: Em: 484 nm, Ex: 375 nm; Resolution Ex: 16 nm, Resolution Em: 16 nm,

EXAMPLE 4

Determination Of TSH By The Release And Measurement Of Alkaline Phosphatase Labeled DTB-AA-16 From A Chromium Dioxide Particle-Anti-TSH IgG1:TSH:Anti-TSH IgG2-Streptavidin~DTB-AA-16-Alkaline Phosphatase Complex 1. Synthesis of DTB-AA-16-Alkaline Phosphatase and DTB-Alkaline Phosphatase The same procedure was used as described in in Example 2.

2. Synthesis of Anti-TSH IgG2-Streptavidin

A preparation of 5 mg streptavidin (Boehringer-Mannheim Biochemicals) was reconstituted with 0.65 mL 0.2M sodium phosphate buffer, pH 8.0. The solution was combined with a 10-fold molar excess of N-succinimidyl-4-(N-maleimidomethyl) cyclo-hexane-1-carboxylate (SMCC; Pierce Co.) and the reaction mixture gently agitated at room temperature for 30 minutes. The solution was loaded onto a Sephadex G-25 column (1.0×30 cm) and then eluted with 0.2M sodium phosphate buffer, pH 6.5. The resulting fractions containing the maleimide-activated streptavidin were collected and pooled.

A 1 mL aliquot of a 10 mg/mL solution of anti-TSH IgG2 (prepared as described in Example 2-1) was dialyzed against 1000 mL 0.2M sodium phosphate buffer, pH 8.0, and held overnight at 4°–8° C. with constant stirring. The solution was transferred to a dark vial and the protein concentration adjusted to 5 mg/mL. The solution was then combined with a 15-fold molar excess of N-succinimidyl S-acetylthioacetate (SATA; Calbiochemical Co.) in dimethyl sulfoxide (DMSO) The reaction mixture was gently agitated at room temperature for 30 minutes. The solution was loaded onto a Sephadex G-25 column (1.0×30 cm), and then eluted with 0.2M sodium phosphate buffer, 6.5. The resulting fractions containing the acetylthioated-anti-TSH IgG2 were collected and pooled.

An aliquot of 2.2 mL of a 1.0 mg/mL solution of the acetylthiolated anti-TSH IgG2 antibody, 1.2 mL of 1.0 mg/mL solution of maleimide-activated streptavidin, and 75 μL of 1M hydroxylamine, pH 7.0, were mixed together simultaneously in a dark vial. The reaction mixture was gently agitated at room temperature for 60 minutes while the reaction was monitored using an HPLC equipped with a GF-250 size exclusion HPLC column (9.4 mm×25 cm; Rockland Co.). The reaction was quenched at room temperature by the addition of 10 μL of 0.1M N-ethylmaleimide (NEM; Aldrich Chemical Co.). After the quenched solution was allowed to sit for 30 minutes, the solution was purified by HPLC using a GF-450 XL size exclusion column (22.5 mm×25 cm; E. I. du Pont de Nemours and Co.). The anti-TSH IgG2-streptavidin was then eluted with 0.2M sodium phosphate buffer with 0.1% sodium azide buffer, pH 7.0 at a flow rate of 2 mL/min. The resulting fractions, which exhibited both biotin binding and immuno-reactivity, were pooled.

The anti-TSH IgG2-chromium dioxide particles were the same as those used in Example 2.

3. Quantitative TSH Immunoassay

Two sets of test tubes were prepared; each tube contained 250 μg chromium dioxide particles onto which anti-TSH IgG1 had been previously immobilized; 500 μL of 2 μg/mL anti-TSH IgG2-streptavidin, and 500 μL of TSH. Test tubes in each set contained concentrations of TSH as follows: 0, 25, and 50 μIU/mL. After incubation at 37° C. for 30 minutes, the chromium dioxide particles were washed three times with Hepes buffer, pH 7.5. Following this, 500 μL of 2 μg/mL DTB-AA-16-alkaline phosphatase was added to one set of test tubes (hereinafter referred to as Set A4), and 500 μL of 2 μg/mL DTB-alkaline phosphatase was added to the other set of test tubes (hereinafter referred to as Set B4-1). Both sets were incubated at 37° C. for 15 minutes and then washed four times with 500 μL of Hepes buffer, pH 7.5.

The test tubes of Set A4 were divided into two identical subsets. Into each test tube of one of the subsets was added 250 μL of a solution of 6.8 mg/mL biotin and 250 μL of the fluorometric substrate 4-methylumbelliferyl phosphate (MUP; Boehringer-Mannheim Biochemicals) in 2.5M DEA to measure the total bound TSH complex. The reaction mixture was incubated at 37° C. for five minutes and the reaction subsequently quenched by the addition of 500 μL of a 0.5M EDTA quenching solution. The particles were then magnetically separated and 100 μL of the supernatants of each test tube was transferred to a clean set of test tubes (hereinafter referred to as Set A4-1). Into each test tube was then added 2.5 mL quenching solution, and the signal generated by the reporter measured using an Aminco fluorometer.

In order to measure the released the DTB-AA-16-alkaline phosphatase, 300 μL of biotin (6.8 mg/mL biotin concentration) was added to the other subset of Set A4 and incubated at 37° C. for ten minutes. The particles were then magnetically separated and 250 μL of the supernatants of each test tube was transferred to a clean set of test tubes (hereinafter referred to as Set A4-2). Following this, 250 μL MUP was added to each tube and the tubes were incubated at 37° C. for five minutes. The reaction was quenched by the addition of a 0.5M EDTA quenching solution. To 100 μL aliquots was added an additional two mL quenching solution and the signal generated by the reporter measured using an Aminco fluorometer.

The test tubes of Set B4, containing the DTB-alkaline phosphatase without the hydrophilic spacer, were treated using the same procedure as that described above for set A4 in order to measure both bound TSH complex (Set B4-1) and released reporter (Set B4-2).

The results of Sets A4 and B4 are shown in Table 4.

TABLE 6

| | TSH CONCENTRATION (μIU/mL) | | |
|---|---|---|---|
| Sample | 0 (F.I.U.) | 25 (F.I.U.) | 50 (F.I.U.) |
| SET A4 (containing DTB-AA-16-alkaline phosphatase) | | | |
| Substrate blank | 86 | — | — |
| Bound Complex (Set A4-1) | 113 | 157 | 216 |
| Released Reporter (Set A4-2) | 101 | 130 | 177 |
| SET B4 (containing DTB-alkaline phosphatase) | | | |
| Substrate blank | 76 | — | |
| Bound Complex (Set B4-1) | 99 | | 86 |
| Released Reporter (Set B4-2) | 86 | | 84 |

F.I.U. = Fluorescensce Intensity Unit
SLM Aminco photon counter 8000C (SLM Instrument, Inc.) Instrument parameter set up as following: Ex/Em = 375/450 nm, Res Ex/Em = 2/2 nm, HV = 850 V, Gain = 100, int. time = 1 sec.

The results in Table 4 indicate that when DTB is directly coupled to alkaline phosphatase without the use of the hydrophilic spacer AA-16, the resulting complex binds less streptavidin-antibody complex than when DTB is linked to alkaline phosphatase via the hydrophilic spacer AA-16.

EXAMPLE 5

Determination of TSH By Release And Measurement Of An Enzyme-Labeled Complex Released From A Solid Support In An Immunoassay Using DTB As A Releasable Ligand Bound To A Hydrophilic Spacer (AA-16) And Streptavidin As A Displacer Ligand Two series of test tubes were prepared; one set containing 500 μL of TSH analyte at a concentration of 0 μIU/mL, and the other set containing 500 μL of TSH analyte at 25 μIU/mL. Into each test tube of both series was added 50 μL of a solution containing 125 μg of chromium dioxide particles, followed by 500 μL of a solution containing 0.5 μg anti-TSH IgG2-AA-16-DTB which had been prepared as described above in Example 2. All test tubes were incubated at 37° C. for 30 minutes with periodic mixing.

The chromium dioxide particles were then separated and washed three times with 500 μL of 250 mM tris, 50 mM sodium bisulfite wash buffer. Into each test tube of both series was added 500 μL of a solution containing 0.001 mg/mL streptavidin-alkaline phosphatase (Chemicon Co.). The tubes were then incubated for 15 minutes at 37° C., the particles separated magnetically and washed four times with 250 mM tris, 50 mM sodium borate wash buffer. To one series of test tubes, 300 μL of biotin (3.0 mg/mL in 250 mM tris, 50 mM sodium borate buffer) was added and, to the other, 300 μL of streptavidin (1 mg/mL in Vista Wash buffer) was added. The tubes were then incubated for 10 minutes at 37° C., followed by separation of the chromium dioxide particles.

A solution of 2.4 mL of MUP/DEA mixture was prewarmed to 37° C. in cuvettes. The reaction was then initiated by the addition of 100 μL of the supernatant from the reaction tubes. RFU readings were taken using an Aminco fluorometer at 0 and 30 seconds. The readings were then subtracted and the difference multiplied by 2 to give the RFU/minute. The results are shown in Table 5.

TABLE 7

| Sample μIU/mL | Biotin released RFU/minute (mean) | Streptavidin released RFU/minute (mean) |
|---|---|---|
| 0 | 0.25 | 0.72 |
| 25 | 45.46 | 30.79 |

Substrate Blank was 0.01 RFU/min

The results in Table 5 indicate streptavidin can be used as displacer ligand to release the reporter, eliminating the need to use biotin in this assay format.

EXAMPLE 6

Effect Of Variant Surface Area On Solid Phase And Released Non-Specific Binding

In order to determine the effect of variant surface area on non-specific binding, two sets of test tubes were prepared in triplicate containing 500 μL of TSH sample at concentrations of 0, 0.05, 0.1, and 50 μIU/mL. Into the replicates of TSH concentration was added 50 μL of solutions of 125 μg, 200 μg, and 250 μg chromium dioxide particles having anti-TSH IgG1 immobilized thereon. Into each of the test tubes, 500 μL of a solution containing 0.5 μg anti-TSH IgG2-AA-16-DTB was added. All samples were incubated at 37° C. for 30 minutes with periodic mixing. Following this, the chromium dioxide particles were separated and washed three times with 500 μL of 250 mM tris, 50 mM sodium borate buffer, pH 7.5. Following the third wash, 500 μL of a 0.001 mg/mL solution of streptavidin-alkaline phosphatase (Chemicon Co.) was added and the react mixtures allowed to incubate at 37° C. for 15 minutes. All tubes were then washed four times with 500 μL 250 mM tris, 50 mM sodium borate wash.

One of the sets of tubes was used to measure released reporter. To this set, 300 μL of a 6.8 mg/mL solution of biotin in 150 mM carbonate buffer was added and the reaction mixture allowed to incubate at 37° C. for 10 minutes. The chromium dioxide particles were then separated and 250 μL of the supernatant of each test tube was removed and transferred to a clean set of tubes (hereinafter referred to as set A5).

To the other set (hereinafter referred to as Set B5), used to measure the solid bound reporter, 250 μL of biotin solution was added to the chromium dioxide particles and the tubes were used without incubation or separation of the supernatant. Into each of the tubes (SET A5 and SET B5) 250 μL of MUP/DEA solution was added and the reaction mixtures incubated at 37° C. for five minutes. The reaction was then quenched by the addition of 5M EDTA quenching solution. Chromium dioxide particles were separated from Set B5 and 100 μL from all tubes was placed in clean cuvettes. Following this, 2.5 mL of quenching solution was added to all the cuvettes to bring the solutions into a range readable by the Aminco fluorometer; measurements were taken at an excitation of 375 nm and an emission of 475 nm. The results are shown in Table 6.

TABLE 8

| Chromium Dioxide Particles (μg) | Surface Area (cm²) | SET B5 (Bound Phase) (F.I.U) | SET A5 (Released Phase) (F.I.U) |
|---|---|---|---|
| 250 | 100 | 0.51 | 0.11 |
| 200 | 800 | 0.49 | 0.12 |
| 125 | 0.30 | 0.30 | 0.11 |

Substrate blank is 0.03

The results in Table 6 indicate that non-specific binding on the solid bound reporter-labeled complex (Set B5) decreases with decreasing surface area. This is known and has been demonstrated in the past with chromium dioxide particles. However, non-specific binding to the released reporter-labeled complex (Set A5) is independent of surface area. This result demonstrates a key advantage provided for by the use of the releasable ligand method of this invention.

What is claimed is:
1. A non-competitive specific binding assay for an analyte comprising the steps of:
   A. preparing an immobilized sandwich structure consisting essentially of:
      1. a solid support having a first binding partner attached thereto wherein the first binding partner is selected from the group consisting of nucleic acid and antibody;
      2. a second binder partner:analyte complex; and
      3. a releasable ligand, wherein said releasable ligand is attached through a temporary bond to a third binding partner having detectable reporter thereon and through a covalent bond to the second binding partner of the second binding partner:analyte complex;
   by contacting said solid support having a first binding partner capable of binding to the analyte attached thereto with:
      1. liquid sample suspected of containing the analyte;
      2. releasable ligand attached through a covalent bond to the second binding partner which is capable of binding to the analyte; and
      3. the third binding partner capable of binding to the releasable ligand and having detectable reporter thereon;
   B. separating the immobilized sandwich structure from soluble components;
   C. breaking the temporary bond by:
      1. adding an excess of a displacer ligand relative to the releasable ligand; or
      2. adding a displacer ligand wherein the affinity of the displacer ligand to the third binding partner is greater than the affinity of the releasable ligand to the third binding partner;
   D. measuring the detectable reporter in solution; and
   E. relating the measured detectable reporter to the amount of analyte in the liquid sample.
2. The non-competitive specific binding assay of claim 1 wherein the releasable ligand is dethiobiotin, the third binding partner is streptavidin and the displacer ligand is biotin.
3. The non-competitive specific binding assay of claim 1 wherein the releasable ligand is streptavidin, the third binding partner is dethiobiotin and the displacer ligand is biotin.
4. The non-competitive specific binding assay of claim 1 wherein the releasable ligand is attached to the second binding partner through a hydrophilic spacer selected from the group consisting of alpha, omega-amino acids and derivatives thereof.

5. A non-competitive specific binding assay for an analyte comprising the steps of:
   A. preparing an immobilized sandwich structure consisting essentially of:
      1. a solid support having a first binding partner attached thereto wherein the first binding partner is selected from the group consisting of streptavidin, avidin and succinylated avidin;
      2. a releasable ligand; wherein said releasable ligand is attached through a temporary bond to the first binding partner; and
      3. a second binding partner:analyte complex, wherein the second binding partner of the second binding partner:analyte complex is attached through a covalent bond to the releasable ligand and the analyte of the second binding partner:analyte complex is attached to a third binding partner having a detectable reporter thereon;
      by contacting said solid support having a first binding partner capable of binding to the releasable ligand attached thereto with:
      1. liquid sample suspected of containing the analyte;
      2. releasable ligand attached through a covalent bond to the second binding partner which is capable of binding to the analyte; and
      3. the third binding partner capable of binding to the analyte and having a detectable reporter thereon;
   B. separating the immobilized sandwich structure from soluble components;
   C. breaking the temporary bond by:
      1. adding an excess of displacer ligand relative to the releasable ligand; or
      2. adding a displacer ligand wherein the affinity of the displacer ligand to the first binding partner is greater than the affinity of the releasable ligand to the first binding partner, wherein the displacer ligand is a ligand that is capable of binding said first binding partner;
   D. measuring the detectable reporter in solution; and
   E. relating the measured detectable reporter to the amount of analyte in the liquid sample.

6. The non-competitive specific binding assay of claim 5 wherein the releasable ligand is selected from the group consisting of biotin, dethiobiotin, iminobiotin and functionalized azo dye and the displacer ligand is selected from the group consisting of biotin and dethiobiotin.

7. The non-competitive specific binding assay of claim 5 wherein the releasable ligand is attached to the second binding partner through a hydrophilic spacer selected from the group consisting of alpha, omega-amino acids and derivatives thereof.

8. A non-competitive specific binding assay for the analyte comprising the steps of:
   A. preparing an immobilized sandwich structure consisting essentially of:
      1. a solid support having a first binding partner attached thereto wherein the first binding partner is selected from the group consisting of nucleic acid and antibody;
      2. an analyte;
      3. a releasable ligand, wherein said releasable ligand is attached through a temporary bond to a second binding partner having detectable reporter thereon and through a covalent bond to the analyte;
      by contacting said solid support having a first binding partner capable of binding to the analyte attached thereto with:
      1. liquid sample suspected of containing the analyte which has been reacted with a releasable ligand which has been activated so that it is capable of covalently binding to the analyte; and
      2. the second binding partner capable of binding to the releasable ligand and having detectable reporter thereon;
   B. separating the immobilized sandwich structure from soluble components;
   C. breaking the temporary bond by:
      2. adding an excess of a displacer ligand relative to the releasable ligand; or
      2. adding a displacer ligand wherein the affinity of the displacer ligand to the second binding partner is greater than the affinity of the releasable ligand to the second binding partner;
   D. measuring the detectable reporter in solution; and
   E. relating the measured detectable reporter to the amount of analyte in the liquid sample.

9. The non-competitive specific binding assay of claim 8 wherein the releasable ligand is selected from the group consisting of biotin, dethiobiotin, iminobiotin and functionalized azo dye; the second binding partner is selected from the group consisting of streptavidin, succinylated avidin and avidin; and the displacer ligand is selected from the group consisting of biotin, dethiobiotin and streptavidin.

10. The non-competitive specific binding assay of claim 8 wherein the releasable ligand is attached to the analyte through a hydrophilic spacer selected from the group consisting of alpha, omega-amino acids and derivatives thereof.

11. A competitive specific binding assay for an analyte comprising the steps of:
   A. immobilizing on a solid support an analyte;
   B. forming an immobilized reporter-labeled complex by contacting the product of step A with a mixture containing reporter-labeled complex prepared by combining:
      1. a liquid sample containing an analyte;
      2. a known quantity of a first binding partner attached through a covalent bond to a releasable ligand, said first binding partner being capable of binding to the analyte; and
      3. a second binding partner having detectable reporter thereon, wherein said second binding partner is capable of being attached through a temporary bond to the releasable ligand;
   C. separating the immobilized reporter-labeled complex from the soluble components;
   D. breaking the temporary bond by:
      1. adding an excess of a displacer ligand relative to the releasable ligand; or
      2. adding a displacer ligand wherein the affinity of the displacer ligand to the second binding partner is greater then the affinity of the releasable ligand to the second binding partner;
   E. measuring the reporter in solution; and
   F. relating the measured detectable reporter to the amount of analyte in the liquid sample.

12. The competitive specific binding assay of claim 11 wherein the releasable ligand is selected from the group consisting of biotin, dethiobiotin, iminobiotin and functionalized azo dye; the second binding partner is selected from the group consisting of streptavidin, succinylated avidin and avidin; and the displacer ligand is selected from the group consisting of biotin and dethiobiotin.

13. The competitive specific binding assay of claim 10 wherein the releasable ligand is capable of being attached to the first binding partner through a hydrophilic spacer selected from the group consisting of alpha omega-amino acids and derivatives thereof.

14. A competitive specific binding assay for an analyte comprising the steps of:
   A. immobilizing on a solid support a first binding partner capable of binding to a releasable ligand through a temporary bond;
   B. forming an immobilized reporter-labeled complex by contacting the product of step A with a mixture containing reporter-labeled complex prepared by combining:
      1. a liquid sample containing the analyte;
      2. a known quantity of a releasable ligand: analyte conjugate wherein the releasable ligand is capable of being attached through a temporary bond to the first binding partner on the solid support; and
      3. a known quantity of a second binding partner capable of binding with the analyte and having detectable reporter thereon;
   C. separating the immobilized reporter-labeled complex from soluble components;
   D. breaking the temporary bond by:
      1. adding an excess of a displacer ligand relative to the releasable ligand; or
      2. adding a displacer ligand wherein the affinity of the displacer ligand to the first binding partner is greater than the affinity of the releasable ligand to the first binding partner, wherein the displacer ligand is a ligand that is capable of binding said first binding partner;
   E. measuring the reporter in solution; and
   F. relating the measured detectable reporter to the amount of analyte in the liquid sample.

15. The competitive specific binding assay of claim 14 wherein the first binding partner is selected from the group consisting of streptavidin, succinylated avidin and avidin; the releasable ligand is selected from the group consisting of biotin, dethiobiotin, iminobiotin and functionalized azo dye; and the displacer ligand is selected from the group consisting of biotin, dethiobiotin and streptavidin.

16. The competitive specific binding assay of claim 14 wherein the releasable ligand is attached to the analyte through a hydrophilic spacer selected from the group consisting of alpha, omega-amino acids and derivatives thereof.

17. A non-competitive specific binding assay for analyte comprising the steps of:
   A. preparing an immobilized sandwich structure consisting essentially of:
      1. a solid support having a first binding partner attached thereto wherein the first binding partner is selected from the group consisting of nucleic acid and antibody;
      2. a second binding partner:analyte complex;
      3. a first releasable ligand, wherein said first releasable ligand is attached through a first temporary bond to a third binding partner and through a covalent bond to the second binding partner of the second binding partner; analyte complex; and
      4. a second releasable ligand having a detectable reporter thereon, wherein said second releasable ligand is attached through a second temporary bond to the third binding partner;
   by contacting said solid support having a first binding partner capable of binding to the analyte attached thereto with:
      1. liquid sample suspected of containing the analyte;
      2. first releasable ligand attached through a covalent bond to the second binding partner;
      3. the third binding partner capable of binding to the first releasable ligand; and
      4. the second releasable ligand capable of binding to the third binding partner and having a detectable reporter thereon;
   B. separating the immobilized sandwich structure from soluble components;
   C. breaking the first and second temporary bonds by:
      1. adding an excess of a displacer ligand relative to the first and second releasable ligand; or
      2. adding a displacer ligand wherein the affinity of the displacer ligand to the third binding partner is greater than the affinity of the first and second releasable ligands to the third binding partner; and
   D. measuring the detectable reporter in solution; and
   E. relating the measured detectable reporter to the amount of analyte in the liquid sample.

18. The non-competitive specific binding assay of claim 17 wherein the first releasable ligand is attached to the second binding partner through a hydrophilic spacer selected from the group consisting of alpha omega-amino acids and derivatives thereof.

19. A competitive specific binding assay for an analyte comprising the steps of:
   A. immobilizing on a solid support an analyte;
   B. forming an immobilized reporter labeled complex by contacting the product of step A with a mixture containing reporter-labeled complex prepared by combining:
      1. a liquid sample containing the analyte;
      2. a known quantity of a first binding partner attached through a covalent bond to a second binding partner, said first binding partner being capable of binding to the analyte; and
      3. a releasable ligand having a detectable reporter thereon, wherein the second binding partner is capable of being attached through a temporary bond to the releasable ligand;
   C. separating the immobilized reporter-labeled complex from the soluble components;
   D. breading the temporary bond by:
      1. adding an excess of a displacer ligand relative to the releasable ligand; or
      2. adding a displacer ligand wherein the affinity of the displacer ligand to the first binding partner is greater than the affinity of the releasable ligand to the first binding partner; and
   E. measuring the reporter in solution; and
   F. relating the measured detectable reporter to the amount of analyte in the liquid sample.

* * * * *